United States Patent
Andersson et al.

(10) Patent No.: US 7,089,070 B1
(45) Date of Patent: Aug. 8, 2006

(54) METHOD AND ARRANGEMENT FOR A SYSTEM FOR MANUFACTURING DENTAL PRODUCTS

(75) Inventors: Matts Andersson, Lerum (SE); Anders Törnquist, Partille (SE)

(73) Assignee: Nobel Biocare AB, Göteborg (SE)

( * ) Notice: Subject to any disclaimer, the term of this patent is extended or adjusted under 35 U.S.C. 154(b) by 278 days.

(21) Appl. No.: 10/130,607

(22) PCT Filed: Nov. 8, 2000

(86) PCT No.: PCT/SE00/02180

§ 371 (c)(1),
(2), (4) Date: May 21, 2002

(87) PCT Pub. No.: WO01/37756

PCT Pub. Date: May 31, 2001

(30) Foreign Application Priority Data

Nov. 26, 1999 (SE) .............................. 9904275

(51) Int. Cl.
*G06F 19/00* (2006.01)
*A61C 5/10* (2006.01)

(52) U.S. Cl. ......................................... 700/99; 433/223
(58) Field of Classification Search ................ 433/223; 700/99, 90, 95, 117; 705/26
See application file for complete search history.

(56) References Cited

FOREIGN PATENT DOCUMENTS

WO 9844865 10/1988

*Primary Examiner*—Leo Picard
*Assistant Examiner*—R Jarrett
(74) *Attorney, Agent, or Firm*—Venable LLP; Eric J. Franklin

(57) ABSTRACT

A manufacturing system for dental products (P, P') operates with coordinating units (9) which receive and register orders from customers (1, 2 and 3). The coordinating units distribute the order to production units (11, 12 and 13). The various units include database whose contents are updated by data replications in conjunction with changes to system functions, system application, system structure, etc. The data contained in the databases of the production units are entered in memory elements which are arranged for accessing program contents when executing data replications via one or more interfaces via which the function for data replications in the system has access or is effected.

16 Claims, 2 Drawing Sheets

METHOD AND ARRANGEMENT FOR A SYSTEM FOR MANUFACTURING DENTAL PRODUCTS

TECHNICAL FIELD

The present invention relates inter alia to a method used in a system for manufacturing dental products, which here include, inter alia, crowns, caps, made of titanium or ceramic material, bridges, etc. The system according to the invention operates with coordinating units or administrative units in which orders from system users, for example dentists and/or dental technicians, are received and registered and are distributed to production units which are intended to manufacture the products in question. The production units are coordinated with and controlled from the coordinating units as a function of the existing order distribution effected in the coordinating or administrative units. The system also operates with so-called data replication for database information (contents) included in the production units and updated as a function of system changes, which can comprise changes to the system functions, the system structure, the system application, customer category divisions, etc. The invention also relates to an arrangement for a manufacturing system for the abovementioned products of tissue-compatible material. The manufacturing system operates in accordance with the above.

PRIOR ART

Reference is made to Swedish Patent 9701309-8 (509148) which relates, inter alia, to an advanced and effective manufacturing system in accordance with the above. In this system, the customers concerned can order products of a technically complex nature and of individual configurations. In accordance with the concept of the system, dentists or dental technicians will themselves be able to execute a query profile for the ordered article. The query form can include information on scanning of a given plaster model, scanning of a given dental situation in a patient's mouth, completion of technical dental data, patient information, details concerning the tooth or tooth part which is to be restored, identification details, type of work the customer wishes to have done by the advanced system PROCERA®, etc. The information can be processed by the dentist and/or dental technician for compilation in a data file with the aid of a program which is used in PROCERA®. Order forms and their transmission can then be effected. It will be appreciated that the advanced manufacturing system PROCERA® is of an especially advanced nature and the system must be able to receive orders from a number of customers and identify the query profiles and produce all or part of the dental products in question and/or give information on how such production can be effected outside the actual PROCERA® system. The coordinating units represent receiving units for the orders and administer the received orders and forward their contents to the production units. The system is designed so that coordinating units can be exchanged and/or added to. The coordinating units work with computers and modem/ISDN connections, and it is within the scope of the known system to be able to arrange computers with different computer power and with different numbers of the said type of connections. In one embodiment, the coordinating unit is constructed as a local network.

The production units thus work with databases to which the coordinating units have access and can cooperate with the production units. The databases work with programs controlling the database contents, and it must be possible for different types of data to be distributed effectively within the system.

DISCLOSURE OF THE INVENTION

Technical Problem

Systems for manufacturing individually and extremely accurately designed dental products/tools are characterized by advanced mechanical constructions and the receipt, distribution and return of large quantities of data to/from the system. Given the complexity and range, the same basic equipment must be able to be used despite constant modernizing and updating requirements placed on system and software. The invention solves this problem, among others.

The advanced manufacturing and information system PROCERA® which is available on the market for provision of advanced individual dental products and provision of information is characterized by a growing network of customers who wish to access the system as subscribers or to use this system for more occasional uses. The system must have a structure permitting constantly increasing (powerful) connection of customer numbers despite the already existing large quantities of data being handled by and distributed within the system. The invention solves this problem too.

In this type of system, it must be possible for updating and improvements to be made done continuously without affecting or disrupting the system. The invention solves this problem too.

In accordance with the above, the system includes databases whose data contents and process-controlling programs have to be updated, changed, improved, etc. To do this, use is made of, inter alia, the abovementioned data replication which involves only relevant data or changes being transmitted to the databases for their adaptation of the data contents to the last-requested update. The databases and their data contents can be largely identical and each update has relatively little effect on the respective database. For disturbance reduction and efficiency of the system, it is necessary that the latter can be designed for or with effective data replication function. The invention solves this problem too.

A large quantity of data can arise if the technical dental information is to be based on scans in Cartesian systems (CAD/CAM), or if the information is to be sent across the Internet and/or IBM network, or if the number of customers is particularly high, which is possible in the case of national systems in which users at widely dispersed locations can be connected to the system.

Certain allocation sequences have previously been made in the updating procedure. The effects from these allocations can be considerably reduced or entirely eliminated by means of the invention.

The use of transport servers for new databases in system constructions needs to be avoided.

Solution

The feature which can principally be regarded as characterizing the novel method according to the invention is that the data contents and any of the said controlling program contents in the databases of the production units are fed to memory elements which are opened for external accessing of the program contents in conjunction with the data replications, and that at least the most important items of the contents of the databases and controlling program contents are arranged to be accessed via one or more connections, for example external interfaces, assigned to the said memory elements, so that data-replicating functions in the system are effected between different units concerned.

In a preferred embodiment, the data contents of the production units can be updated between the said units concerned via connections or exposed interfaces, connetion being effected to the public telephone network and/or computer network of the coordinating units and production units. The databases of the coordinating units and/or control software can also be updated via exposed connections or interfaces from an updating unit.

An arrangement according to the invention can principally be regarded as being characterized by the fact that the data contents and any program contents in the databases of the production units are entered in memory elements, and that the memory elements are arranged for external accessing of data contents or program contents upon or for implementation of the said data replications via one or more connections or external interfaces, via which the data replications can be effected.

In further developments of the inventive concept, the databases of the production units have essentially the same or corresponding contents and the same applies to the controlling program contents in the different databases. In one embodiment, the data replications can be effected by means of essentially parallel actuations of data contents or controlling program contents in the memory elements of the databases. Alternatively, updating can take place sequentially in the different memory elements, or updating of first content items can be updated before second content items, etc.

In further developments of the inventive concept, after each data replication has been effected, the said coordinating units can be run together with the databases of the production units with respect to manufacture, system administration, etc. In one embodiment, the data contents in the databases can relate to arrival of data files initiated by the orderer, finance details relating to costs connected with the given product, data file contents, file preparations, product administration, milling or ceramic material registration and/or orderer addresses. The said data contents can thus be acted on by the updated controlling program contents. The production units can be connected to transport servers. The databases of the production units can preferably comprise data contents related to ceramic production of products, for example caps, where the data contents also relate to the composition of the ceramic material, the selection and/or treatment upon production. The contents of the databases can differ between different ceramic materials of different types or manufacturers. In one embodiment, the contents of the databases are related to semi-finished products (i.e. only part of the product is manufactured) which are intended for cooperation with further products or tools produced in the system, for example a ceramic cap whose production is based on the design of the tool punch.

Advantages

The features which have been proposed above provide possibilities for an effective and economically advantageous updating function in the system which, as a result, can be constantly expanded within wide limits and for large resources, without the normal operation of the system needing to be disrupted or interrupted on account of the updates, which can be constantly repeated or can be substantially continuously ongoing. Connection to and cooperation with coordinating units included in the system can take place in the system after each update or change to the system. The invention permits more long-lasting efficiency and speed of updating and system expansion. The existing contents of the databases can be added to and modified within wide limits. Conventional programs and programming languages can be used for the function and administration controls within the system, whose products can include milled products/tools, pressed and sintered ceramic caps, etc. Previously conventional techniques can be retained in the system, and thus SQL (Structured Query Language) can be retained and used as the control and administration language. The information contents can relate to scanning of plaster models, dental data, patient, tooth type, ID type, type of work, etc., in accordance with before. The invention permits rapid access to the data contents which are to be data-replicated. On account of the fact that the computer equipment as such does not need to be engaged in handshake procedures on requested access to data contents for updating thereof, the problems of disruption and delay in said updates are reduced. A host computer can update the production unit(s). This applies also to the coordinating unit(s). The event tables used are modified and replicated directly across to the other units concerned (serial actuation). Information items or data in the tables are introduced, modified and/or removed, and the amendments in the tables are transferred across to each other in serial actuation within the system. The updates can be effected automatically or at certain time intervals. Reconstructions can therefore be made effectively a short time after crashing. A host computer represents a source and doublet on a database. Each item in the system has a host database in the register database of the production unit. There is also a host database for customer categories, etc. By means of tables which update sequentially and reconstructions of databases, advantages are also achieved from other aspects, such as back-up, dynamics, etc.

DESCRIPTION OF THE FIGURES

A presently proposed method and arrangement using the characteristic features of the invention will now be described with reference to the attached drawings, in which.

DETAILED EMBODIMENT

Figure 1:
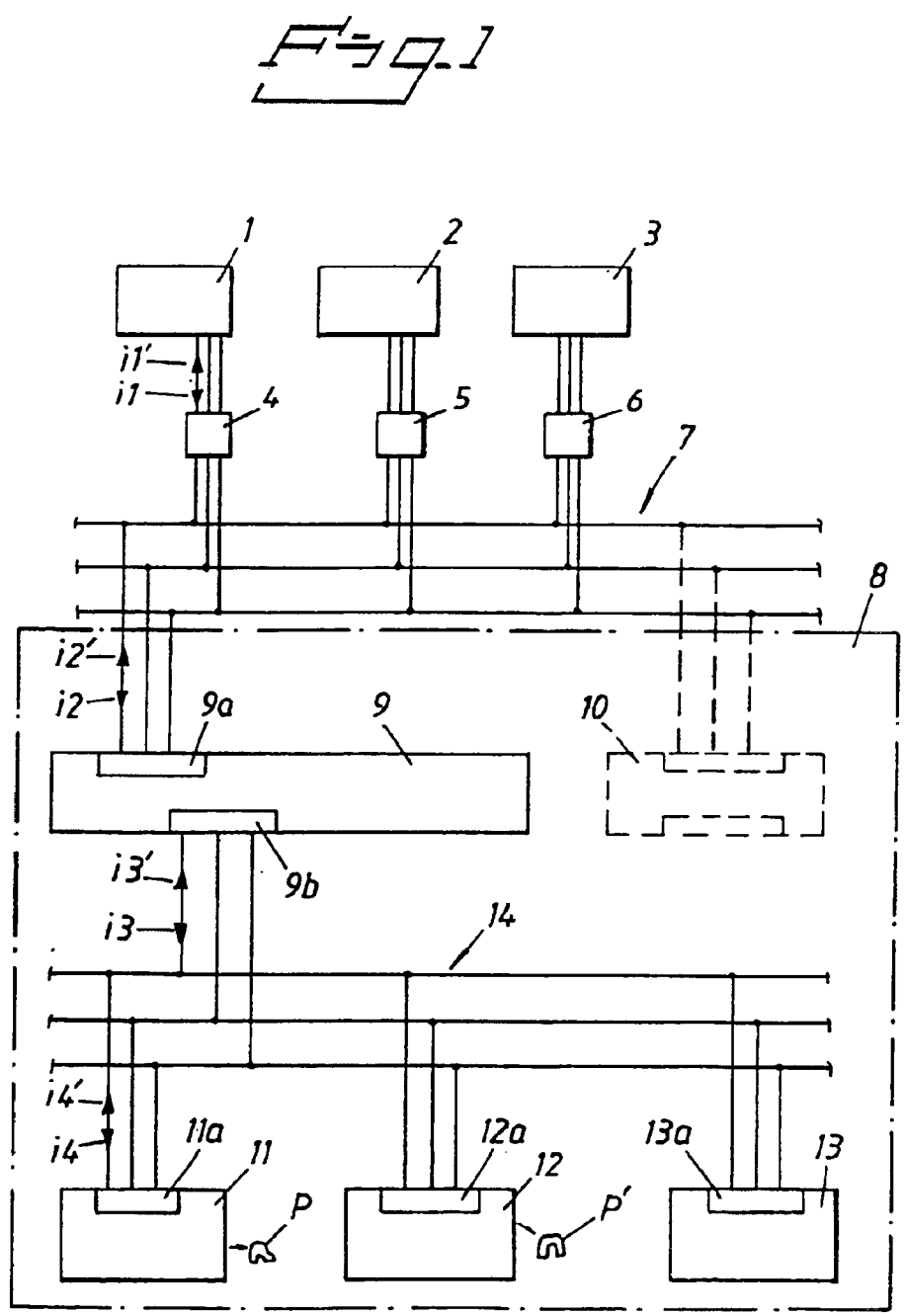
FIG. 1 is a block circuit diagram showing the basic structure of the earlier system.

In FIG. 1, users 1, 2 and 3 can be connected via modem equipment 4, 5 and 6, respectively, to a telephone network and/or computer network, which can entirely or partially comprise the Internet and/or the so-called IBM network. The said customers, who include geographically wide-spread (other ends of a country, other countries, etc.) dentists and/or dental technicians can compile query and order profiles in accordance with the above. The said orders are sent to the advanced central manufacturing system PROCERA®, which is connected to the network 7 via coordinating units 9 which administer the receipt of the orders. The coordinating unit 9 is provided with modem connections 9*a*. The coordinating units can be one or more in number, the situation with several coordinating units in FIG. 1 being indicated by 10 which symbolizes a second coordinating unit. Further coordinating units can be included in the same way. The coordinating units can cooperate or run together with production units 11, 12 and 13, and the cooperation with these takes place via a local network 14 consisting of a local area network of the LAN type. The production units are connected to the network 14 via connection elements 11a, 12a and 13a, respectively.

Each customer 1, 2 or 3 can thus initiate a query profile or an order, which for customer 1 has been symbolized by $i_1$. Each coordinating unit, for example the coordinating unit 9, receives the order transmitted via the customer's modem 4 and the public network 7, the signal received in the coordinating unit 9 being indicated by $i_2$. The coordinating unit 9 receives the orders from the customers, registers these, and effects a distribution within the system which relates to the orders in question. The coordinating unit also has an adapter unit 9b via which the coordinating unit cooperates with and controls the production unit 11, 12 and 13, the output signal from the unit 9b being indicated by $i_3$. The production unit 11 in question receives the distribution signal 9 from the coordinating unit concerned, the signal to the unit 11a being indicated by $i_4$. The production unit then effects the actual order which can involve a dental product in accordance with the above. The dental product is returned physically to the customer 1 in a manner known per se. Alternatively, the query profile from the customer can include a request for information from the system, and the said information can be returned in the system, for example from the coordinating unit 9 and/or the production unit concerned, e.g. 11. The signals returned in this way are indicated by $i_1'$, $i_2'$, $i_3'$ and $i_4'$.

Figure 2:
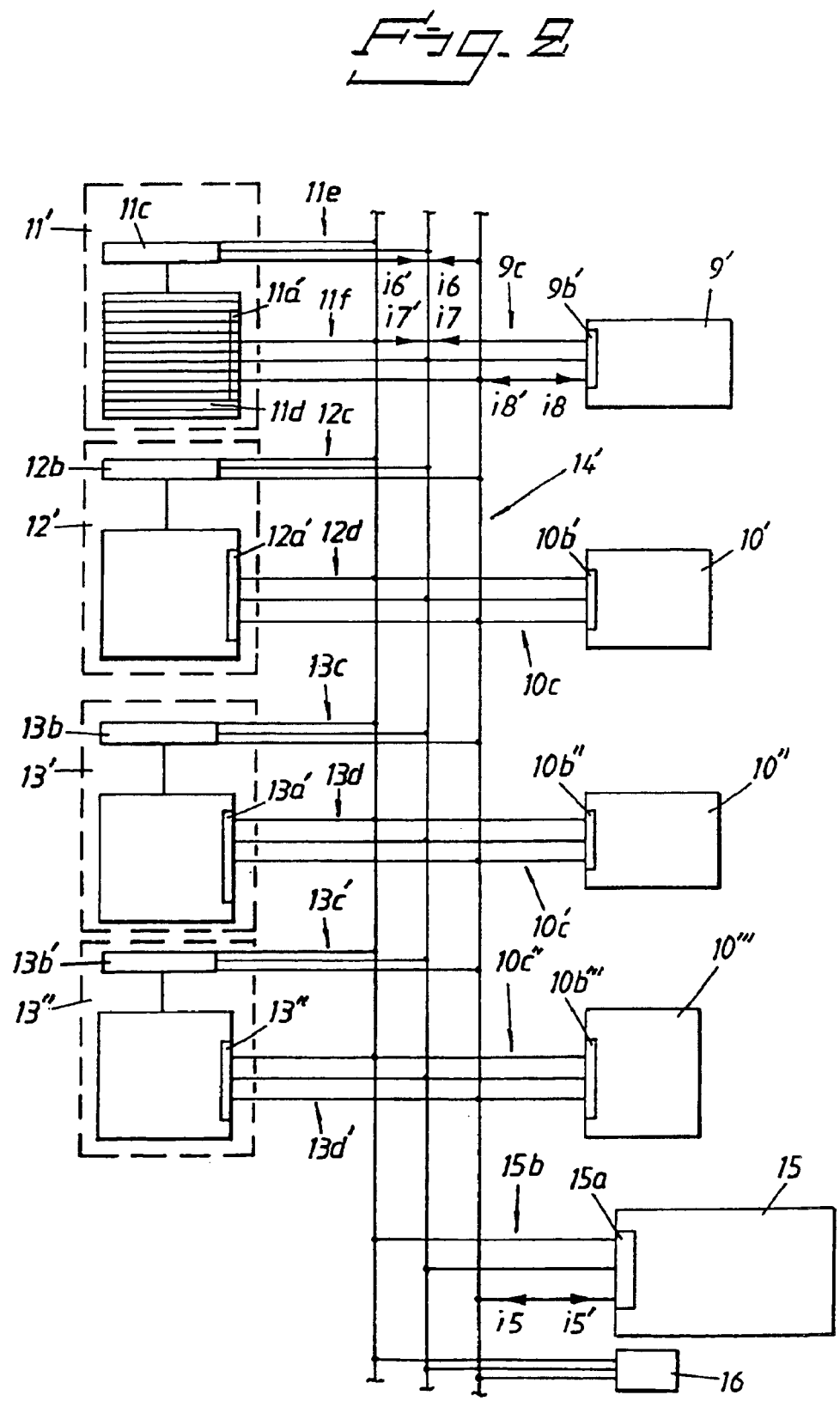
FIG. 2 is a block circuit diagram showing the interaction between coordinating units and production units and the updating function for table contents/data contents and the control programs in databases of the production units.

FIG. 2 shows four coordinating units 9', 10', 10" and 10'". The said coordinating units have connection elements 9b', 10b', 10b" and 10'", respectively, to the internal or local network 14' (cf. 14 according to FIG. 1). Similarly, four production units are indicated by 11', 12', 13' and 13". The connections to the network 14' are in this case indicated by 11a', 12a', 13a' and 13a". The production units work with data contents or databases, the database for production unit 11' being indicated by 11d. The other production units are provided with databases which are identical or substantially equivalent to the said database 11d. The database can contain data in different files, for example files with data for file entry, financial data, manufacturing data files, file preparation data, production administration data, milling coordinates registration data, ceramic material selection data, delivery address data, etc. The production units are also assigned memory elements 11c, 12b, 13b and 13b'. The memory elements include data contents and software of types known per se, in which respect reference is made, inter alia, to SQL databases in accordance with the above. The memory elements are connected directly to the local computer network 14' via connections or interfaces 11e, 12c, 13c and 13c'. These interfaces are thus exposed to the network structure 14'. The databases 11d in the production units are connected to the network 14' via interfaces 11f, 12d, 13d and 13d'.

The databases in the production units can be regarded as production databases. The coordinating units 9', 10', 10" and 10'" are provided with so-called application databases which also comprise data contents and use SQL. The application databases in the coordinating units can be run together with the database arrangement in the production units. Thus, the coordinating units can comprise or involve data on finance reports, dental specifications, article index, customer index, client registration, client databases, production modifications. The data in the bases are arranged in tables which must be updated successively by reciprocal serial actuation in a known manner.

By means of the arrangement proposed above, the data contents or the tables in the databases and their control programs can be updated in an effective manner by means of known data replication functions in the public or local network 14'. The updating or data replication can take place sequentially or successively in the various units concerned. Alternatively, or in addition to this, different parts of the database contents can be replicated before other database parts, etc. The interfaces or connections for the units 9', 10', 10", 10'" in FIG. 2 are symbolized by 9c, 10c, 10c' and 10c", respectively. The database contents and software in the last-mentioned coordinating units are updated in a manner known per se via their connections or interfaces exposed to the network.

The system also includes an updating unit 15 (for example one or more host computers) for the said database contents and programs controlling the databases. The unit 15 is provided with a connection nit 15a to the network 14' via an interface 15b. By means of the structure shown, the updating unit 15 has, via its interface, direct access on the one hand to the interfaces 11e, 12c, 13c and 13c', respectively, of the databases in the production units and, on the other hand, to the program contents in the memory elements 11c, 12b, 13b and 13b' via the said interfaces.

Referring to the embodiment according to FIG. 2, the coordinating units 9', 10', 10" and 10'" can be designed with external memory elements corresponding to those (11c, 12b, 13b, 13b') for the production units. However, memory elements can be arranged internally within the units 9', 10', 10" and 10'" and are exposed, in a similar way to the memory elements of the production units, via the interfaces 9c, 10c, 10c' and 10c", respectively. Correspondingly, the external memory elements 11c, 12b, 13b and 13b' can be integrated in the production units in the same way as in the case of the coordinating units. In FIG. 1, dental products in the form of caps produced by the production units 11 and 12 are indicated by P and P'.

In FIG. 2, a data replication function or data replication start from the updating unit 15 is represented by $i_5^*$. The data replication can be directed towards the contents in the memory elements 11c, whose received signals from the public network 14' are indicated by $i_6$. Alternatively, or in addition to this, the replication can involve updating of the contents in the production unit concerned, for example 11d, the signal received from the network 14' by the production unit in question in this case being designated by $i_7$. Alternatively, or in addition to this, the databases or software programs in the coordinating units can be updated, the signal received from the public network 14' in this case being indicated by $i_8$. In the event of communication taking place in two directions upon replication, the updating unit 15 can receive signals $i_5'$ which have been initiated from $i_6'$, $i_7'$ and $i_8'$ from the respective element and/or unit concerned. FIG. 2 also includes ne or more transport servers 16.

A modification in a table in a first unit 11', 12', 13', etc., or 9', 10', 10", etc., of the said type can induce replication of the modification across to a second unit of the said listed units, and thereafter replication of the modification across to a third unit of the said units, and so on. A subsequent modification is handled in the same way, and so on. See also the host computer arrangement as described above.

The invention is not limited to the embodiment described above by way of example, but can be modified within the scope of the attached patent claims and the inventive concept. A data replication in a table can be caused by the event (events) insert, replace, change, in which case the table includes the event number, time of the event, data concerned, why the event takes place, etc. The events can be caused by customer application, system change, etc. The system can operate with order registration, file registration, address registration which gives order events, file/address events, etc., to the coordinating units or a system section (router) which in turn can create follow-up events and product/production events for a user interface in the system. It will be appreciated that a very large number of events are created in the PROCERA® system, given the great machine capacity, customer base, data quantity, etc., with which the system operates. It will also be appreciated that a very large quantity of data is replicated between the different units and that, for example, handshake procedures would not be an economic solution. The large quantity of data is increased with the transmission capacity in the communications systems which can permit information transfer caused by photo and laser scans and CAD/CAM techniques in the machinery producing the products.

Further events via the product database system between routers in interfaces between which the database is arranged can be finance actions, preparation actions, milling coordinates actions, etc. The system can also include material, product and component registers which need to be updated.

What is claimed is:

1. A method for manufacturing dental products, the method comprising:

receiving orders from system users with at least one coordinating unit;

registering the orders with the at least one coordinating unit;

distributing the orders with at least one coordinating unit to production units;

running the production units together with and controlled from the coordinating unit as a function of existing order distribution and with data replications for databases that are included in the production units and the coordinating units;

updating the databases of the production units and the coordinating units as a function of at least one of events and system changes, wherein the updating is carried out with an updating unit comprising an interface operable to be connected to at least one of a public telephone network and a computer network;

feeding data to databases with memory elements that are exposed for accessing the data contents in conjunction with the data replications;

arranging at least selected portions of the contents of the databases to be accessing via at least one connection or interface assigned to the memory elements; and effecting data replication through the connections or interfaces.

2. A system for oral rehabilitation, the system comprising:

coordinating units operable to receive and register dental product order data from customers and distribute the order data to production units, the coordinating units comprising memory elements operable to store databases comprising the order data;

production units operable to receive the order data from the coordinating units and comprising memory elements operable to store the order data and databases operable to control of production of dental products;

circuitry operable to replicate at least portions of the databases in the coordinating units and production units;

at least one connection among the memory elements of the coordinating units and production units, wherein the connection is operable to transmit replicated data throughout the system; and an updating unit operatively connected to the production units and the coordinating units and operative to update databases of the production units and the coordinating units, wherein the updating unit comprises an interface operable to be connected to at least one of a public telephone network and a computer network.

3. The system according to claim 2, wherein the data replications are operable to implement at least one of events and system changes through the at least one connection.

4. The system according to claim 3, wherein the system changes are selected from the group consisting of changes to system functions, system application, system structure, and customer categories.

5. The system according to claim 2, wherein the order data comprises specifications for dental products.

6. The system according to claim 2, wherein the at least one connection comprises at least one member of the group consisting of a local area network and the internet.

7. The system according to claim 2, wherein producing the dental products comprises delivery of previously produced dental products and production of dental products utilizing order data.

8. The system according to claim 2, wherein the databases comprise at least one of data for file entry, financial data, manufacturing data files, file preparation data, production administration data, milling coordinate registration data, ceramic material selection data, delivery address data finance report data, dental specification data, article index data, customer index data, client registration data, client databases, production modification data, financial data concerning costs of a dental product, file preparation data, product administration data, milling data, ceramic registration data, and orderer addresses.

9. The system according to claim 2, wherein the at least one connection is operable to permit remote updating of the databases.

10. The system according to claim 2 wherein each production unit and each coordinating unit comprises a database, and wherein data is replicated in all databases to provide each database with similar contents.

11. The system according to claim 2, wherein the dental products are ceramic and the databases comprise ceramic product production data comprising at least one of composition and treatment data for ceramic material upon production.

12. The system according to claim 11, wherein the ceramic products comprise caps.

13. The system according to claim 11, wherein the contents of the databases varies depending upon the type of ceramic material.

14. The system according to claim 11, wherein the databases comprise semi-finished product data operable to cooperate with products or tool produced by the system.

15. The system according to claim 14, wherein the semi-finished product comprises a ceramic cap the production of which is based on a tool punch.

16. The system according to claim 2, wherein the at least one connection comprises an exposed interface operable to update data contents of at least one of the production units and the coordinating units via the data replications.

* * * * *